US012589126B2

(12) United States Patent
Sohn et al.

(10) Patent No.: US 12,589,126 B2
(45) Date of Patent: Mar. 31, 2026

(54) **COMPOSITION OF STIMULATING IMMUNITY COMPRISING *LACTOBACILLUS RHAMNOSUS* LM1019 AND STARTER STRAINS**

(71) Applicants: LACTOMASON CO., LTD., Jinju-si (KR); BINGGRAE CO., LTD., Namyangju-si (KR)

(72) Inventors: Minn Sohn, Jinju-si (KR); Je Seong Park, Gwangju-si (KR); Ye Ji You, Siheung-si (KR); Young Sup Shin, Seoul (KR); Sung Hwan Kim, Yongin-si (KR); Chul Hong Kim, Seongnam-si (KR)

(73) Assignees: LACTOMASON CO., LTD., Jinju-si (KR); BINGGRAE CO., LTD., Namyangju-si (KR)

( * ) Notice: Subject to any disclaimer, the term of this patent is extended or adjusted under 35 U.S.C. 154(b) by 192 days.

(21) Appl. No.: 18/419,725

(22) Filed: Jan. 23, 2024

(65) Prior Publication Data
US 2024/0307468 A1    Sep. 19, 2024

(30) Foreign Application Priority Data
Mar. 17, 2023    (KR) ........................ 10-2023-0034911

(51) Int. Cl.
| | |
|---|---|
| *A61K 35/747* | (2015.01) |
| *A23C 9/123* | (2006.01) |
| *A61K 35/744* | (2015.01) |
| *A61K 35/745* | (2015.01) |
| *C12N 1/20* | (2006.01) |
| *C12N 1/205* | (2026.01) |
| *C12R 1/225* | (2006.01) |

(52) U.S. Cl.
CPC .......... *A61K 35/747* (2013.01); *A23C 9/1234* (2013.01); *A61K 35/744* (2013.01); *A61K 35/745* (2013.01); *C12N 1/205* (2021.05); *A23V 2400/113* (2023.08); *A23V 2400/123* (2023.08); *A23V 2400/175* (2023.08); *A23V 2400/249* (2023.08); *A23V 2400/531* (2023.08); *C12R 2001/225* (2021.05)

(58) Field of Classification Search
CPC .. A61K 35/747; A61K 35/744; A61K 35/745; A23C 9/1234; C12N 1/205; C12N 1/20; A23V 2400/113; A23V 2400/123; A23V 2400/175; A23V 2400/249; A23V 2400/531; C12R 2001/225; Y02A 50/30
See application file for complete search history.

(56) References Cited

FOREIGN PATENT DOCUMENTS

| | | |
|---|---|---|
| KR | 10-2014-0037544 A | 3/2014 |
| KR | 10-1832357 B1 | 2/2018 |
| KR | 10-1864347 B1 | 6/2018 |
| KR | 10-2056916 B1 | 12/2019 |
| KR | 10-2166461 B1 | 10/2020 |
| KR | 10-2168310 B1 | 10/2020 |
| KR | 10-2296286 B1 | 9/2021 |
| KR | 10-2443495 B1 | 9/2022 |

OTHER PUBLICATIONS

L. Laterza, G. Gibiino, F. Scaldaferri, A. Gasbarrini, Benefits of multistrain bacteria formulations for health, Journal of Functional Foods, vol. 47, 2018, pp. 531-546, ISSN 1756-4646, doi.org/10.1016/j.jff.2018.05.051. (Year: 2018).*

* cited by examiner

*Primary Examiner* — Kade Ariani
(74) *Attorney, Agent, or Firm* — NKL LAW; Jae Youn Kim

(57) ABSTRACT

The present disclosure relates to an immune-enhancing composition comprising *Lactobacillus rhamnosus* LM1019 and starter strains. An immune-enhancing composition comprising *Lactobacillus rhamnosus* LM1019 and starter strains according to the present disclosure has an excellent immune-enhancing effect by increasing the amount of nitric oxide (NO) produced and improving the TNF-α secretion ability. Also, since the immune-enhancing composition contains the starter strain, it can be used to produce fermented milk. Under the provisions of the Budapest Treaty on the International Recognition of the Deposit of Microorganisms for the Purposes of Patent Procedure, the *Lactobacillus rhamnosus* LM1019 strain was deposited with the international depositary authority: the Korean Culture Center of Microorganisms (KCCM) on Aug. 11, 2017, under the Accession Number: KCCM12308P.

6 Claims, 2 Drawing Sheets

COMPOSITION OF STIMULATING IMMUNITY COMPRISING *LACTOBACILLUS RHAMNOSUS* LM1019 AND STARTER STRAINS

CROSS-REFERENCE TO RELATED APPLICATION

This application claims the benefit under 35 USC 119(a) of Korean Patent Applications No. 10-2023-0034911 filed on Mar. 17, 2023, in the Korean Intellectual Property Office, the entire disclosures of which are incorporated herein by reference for all purposes.

TECHNICAL FIELD

The present disclosure relates to an immune-enhancing composition comprising *Lactobacillus rhamnosus* LM1019 and starter strains, and more particularly, to a composition comprising *Lactobacillus rhamnosus* LM1019 and starter strains that can be used to produce fermented milk and also has an immune-enhancing effect.

BACKGROUND

Probiotics are known to confer a health benefit on the host when consumed in an appropriate amount. Also, probiotics are known to have antioxidant, anti-inflammatory, cholesterol-lowering and anti-diabetic effects which have been reported to vary depending on the strain. Further, as the demand for immunity is filled with needs for probiotics, the functions of lactic acid bacteria fermentation are being reexamined.

Meanwhile, immunity is a self-defense system present in the body and a procedure in which various kinds of materials or organisms invading from the outside of the body are recognized as foreign substances against one's own body and then eliminated and metabolized. The immunity protects the body from the damage caused by external stimulation or invasion of pathogenic microorganisms, but like an inflammatory response, the immunity may also damage one's own tissues. The improvement of immune function is an action of regulating changes in immune function to restore the immune function to normality or decrease fluctuations and is divided into the inhibition of immune function or the enhancement of immune function. The mitigation of hypersensitive immune response refers to inhibiting an undesirably increased immune response, such as an allergic reaction caused by an adverse reaction to a foreign substance or a response to a self-antigen or a modified self-antigen.

To overcome the occurrence of immune function disorders caused by various factors, various immune enhancers and immunotherapeutic agents are being used, but have various problems such as side effects. Accordingly, there is a need for an immune-enhancing composition that can be taken for a long period of time without side effects and is also suitable for prevention.

Accordingly, the present inventors have made extensive efforts to develop a composition that can be taken for a long period of time without side effects and can also help enhance immunity, and have completed the present disclosure by developing a composition comprising a mixed strain that can be used to produce fermented milk and also has an immune-enhancing effect.

SUMMARY

In view of the foregoing, the present disclosure is conceived to provide an immune-enhancing composition comprising *Lactobacillus rhamnosus* LM1019 and starter strains that can be used to produce fermented milk and also has an immune-enhancing effect.

However, the problems to be solved by the present disclosure are not limited to the above-described problems. Although not described herein, other problems to be solved by the present disclosure can be clearly understood by a person with ordinary skill in the art from the following descriptions.

A first aspect of the present disclosure provides a composition comprising mixed strain comprising *Lactobacillus rhamnosus* LM1019 and starter strains.

A second aspect of the present disclosure provides a food composition comprising *Lactobacillus rhamnosus* LM1019 and starter strains.

A third aspect of the present disclosure provides a pharmaceutical composition for preventing or treating immune-related diseases, comprising *Lactobacillus rhamnosus* LM1019 and starter strains.

An immune-enhancing composition comprising *Lactobacillus rhamnosus* LM1019 and starter strains according to the present disclosure has an excellent immune-enhancing effect by increasing the amount of nitric oxide (NO) produced and improving the TNF-α secretion ability. Also, since the immune-enhancing composition contains the starter strain, it can be used to produce fermented milk.

BRIEF DESCRIPTION OF THE DRAWINGS

In the detailed description that follows, embodiments are described as illustrations only since various changes and modifications will become apparent to a person with ordinary skill in the art from the following detailed description. The use of the same reference numbers in different figures indicates similar or identical items.

DETAILED DESCRIPTION

Figure 1:
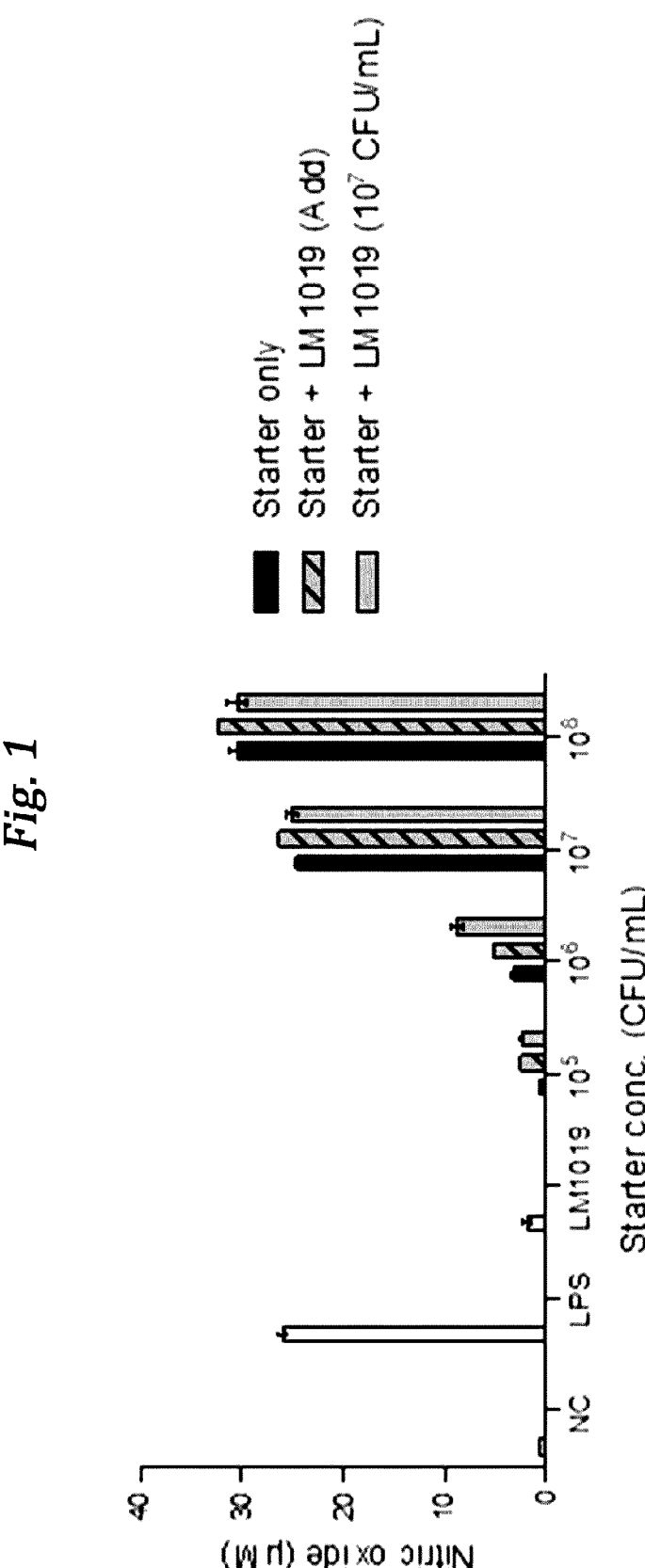
FIG. 1 shows the result of confirming the nitric oxide (NO) production effect of *Lactobacillus rhamnosus* LM1019, starter strains, and mixtures thereof.

Hereafter, examples of the present disclosure will be described in detail with reference to the accompanying drawings so that the present disclosure may be readily implemented by a person with ordinary skill in the art. However, it is to be noted that the present disclosure is not limited to the examples but can be embodied in various other ways.

Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise.

Through the whole document, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Through the whole document, the term "combination(s) of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

A first aspect of the present disclosure provides a composition comprising a mixed strain comprising *Lactobacillus rhamnosus* LM1019 and starter strains. Under the provisions of the Budapest Treaty on the International Recognition of the Deposit of Microorganisms for the Purposes of Patent Procedure, strain *Lactobacillus rhamnosus* LM1019 was deposited with the international depositary authority: the Korean Culture Center of Microorganisms (KCCM) on Aug. 11, 2017 under the accession number KCCM12308P.

In an embodiment of the present disclosure, the starter strains may consist of *Streptococcus thermophilus, Lactobacillus delbrueckii* subsp. *bulgaricus, Lactobacillus acidophilus*, and *Bifidobacterium lactis*.

According to an embodiment of the present disclosure, a concentration of *Lactobacillus rhamnosus* LM1019 (KCCM 12308P) in the mixed strain may be $10^5$ CFU/mL to $10^8$ CFU/mL, preferably $10^7$ CFU/mL, but is not limited thereto.

According to an embodiment of the present disclosure, a concentration of the starter strains in the mixed strain may be $10^5$ CFU/mL to $10^8$ CFU/mL, preferably $10^6$ CFU/mL, but is not limited thereto.

According to an embodiment of the present disclosure, when a concentration of *Lactobacillus rhamnosus* LM1019 (KCCM 12308P) in the mixed strain is $10^7$ CFU/mL and a concentration of the starter strains in the mixed strain is $10^6$ CFU/mL, it is confirmed as a result of test to verify the immune effect that a mixture of *Lactobacillus rhamnosus* LM1019 and the starter strains at the above-described concentrations has a better effect than a mixture in which *Lactobacillus rhamnosus* LM1019 and each of the starter strains are simply added and thus exhibits a synergetic effect.

In an embodiment of the present disclosure, the mixed strain may have an immune-enhancing effect and may be contained in various compositions such as a food composition, a health functional food composition and a pharmaceutical composition for enhancing immunity.

A second aspect of the present disclosure provides a food composition comprising *Lactobacillus rhamnosus* LM1019 and starter strains. The features described above in respect of the first aspect of the present disclosure may equally apply to the food composition according to the second aspect of the present disclosure.

In an embodiment of the present disclosure, the food composition may contain a strain of *Lactobacillus rhamnosus* LM1019 and starter strains, live bacteria, heat-killed bacteria, culture fluid, fragments and/or extracts thereof.

In an embodiment of the present disclosure, the starter strains may consist of *Streptococcus thermophilus, Lactobacillus delbrueckii* subsp. *bulgaricus, Lactobacillus acidophilus*, and *Bifidobacterium lactis*.

Through the whole document, the term "heat-killed bacteria" is opposite to the term "live bacteria" and refers to bodies obtained by suppressing the growth of bacteria such as heat-treating live bacteria obtained by fermentation and metabolites thereof. The heat-killed bacteria may contain cytoplasm, cell wall, antibacterial substances such as bacteriocin, polysaccharides, organic acid, and the like. Products using the heat-killed bacteria have higher stability than live bacteria products and are particularly excellent in heat resistance and have high stability to the external environment. Therefore, the products using the heat-killed bacteria are easier to store and have longer shelf life than the existing live bacteria products. Further, since the regulations on the use of antibiotics become stricter, there are a handful of companies that have produced heat-killed bacteria products. Therefore, considering the application as substitutes and the number of the producing companies, the marketability and growth potential is remarkably high.

Through the whole document, the term "culture fluid" refers to a substance obtained by culturing the strain of the present disclosure in a known liquid medium or solid medium and may be interchangeably used with "culture medium".

Through the whole document, the term "food" may include meats, sausages, breads, chocolates, candies, snacks, cookies, pizza, ramens, other noodles, gums, dairy products including ice cream, soups, beverages, teas, drinks, alcohol drinks, vitamin complexes, health functional foods and health foods, and may include all foods in the accepted meaning.

Through the whole document, the term "health functional food" refers to foods prepared and processed using raw materials or ingredients having useful functions to the human body in accordance with the Health Functional Food Act, No. 6727, and the "functionality" refers to adjusting nutrients on a structure and a function of the human body or obtaining a useful effect for health such as a physiological action.

The food of the present disclosure can be manufactured by conventional methods used in the art, and can be manufactured by adding conventional raw materials and ingredients used in the art. Further, a formulation of the food is not limited as long as the formulation is accepted as a food. The food composition of the present disclosure may be prepared in a variety of formulations. Since the food is used as raw materials, unlike general drugs, the food composition is free from side effects which may occur when a drug is taken for a long time and may have excellent portability.

The food composition may further contain a physiologically acceptable carrier. The kind of the carrier is not particularly limited. Any carrier may be used as long as it is commonly used in the art.

Further, the food composition may further contain additional ingredients that are commonly used in food compositions so as to improve smell, taste, visuality, etc. For example, the food composition may contain vitamins A, C, D, E, B1, B2, B6, B12, niacin, biotin, folate, pantothenic acid, etc. Furthermore, the food composition may also contain minerals such as zinc (Zn), iron (Fc), calcium (Ca), chromium (Cr), magnesium (Mg), manganese (Mn), copper (Cu), chromium (Cr), etc. In addition, it may also contain amino acids such as lysine, tryptophan, cysteine, valine, etc.

The food composition of the present disclosure may be used as, for example, a health beverage composition, and in this case, the health beverage composition may further contain various flavors or natural carbohydrates, as in common beverages. The natural carbohydrates may include monosaccharides, disaccharides, polysaccharides, and sugar alcohols. The sweeteners may be natural sweeteners such as thaumatin or a stevia extract; or synthetic sweeteners such as saccharin or aspartame.

In addition, the health beverage composition may contain various nutrients, vitamins, minerals, flavors, colorants, pectic acid and salts thereof, alginic acid and salts thereof, organic acid, protective colloidal thickeners, pH regulators, stabilizers, antiseptics, glycerin, alcohols, or carbonating agents. Moreover, the health beverage composition may contain fruit flesh used to prepare natural fruit juices, fruit juice beverages or vegetable beverages.

In an embodiment of the present disclosure, the food composition may be a health functional food composition.

A third aspect of the present disclosure provides a pharmaceutical composition for preventing or treating immune-related diseases, comprising *Lactobacillus rhamnosus* LM1019 and starter strains. The features described above in respect of the first and second aspects of the present disclosure may equally apply to the pharmaceutical composition according to the third aspect of the present disclosure.

In an embodiment of the present disclosure, the pharmaceutical composition may contain a strain of *Lactobacillus rhamnosus* LM1019 and starter strains, live bacteria, heat-killed bacteria, culture fluid, fragments and/or extracts thereof.

In an embodiment of the present disclosure, the starter strains may consist of *Streptococcus thermophilus, Lactobacillus delbrueckii* subsp. *bulgaricus, Lactobacillus acidophilus*, and *Bifidobacterium lactis*.

In an embodiment of the present disclosure, the term "immune-related disease" refers to at least one selected from the group consisting of tuberculosis, pneumonia, peritonitis, urinary tract infection, meningitis, myopericarditis, encephalitis, measles, hepatitis, sepsis, bubonic plague, leprosy, syphilis, tetanus, anthrax, actinomycosis, botulism, *Clostridium difficile*-induced colitis, food poisoning, gas gangrene, tetanus, brucellosis, cholera, Legionnaires' disease, pertussis, bacillary dysentery, tularemia, typhoid fever, smallpox, chickenpox, shingles, COVID-19, SARS, MERS, dengue, yellow fever, Zika virus infection, Ebola virus disease, influenza, cold, avian influenza, hand-foot-mouth disease, acquired immunodeficiency syndrome (AIDS), and malaria.

Through the whole document, the term "treat" refers to all activities improving or enhancing an immune-related disease by administering a pharmaceutical composition comprising a mixed strain of the present disclosure as an active ingredient to a subject with an immune-related disease.

In an embodiment of the present disclosure, the pharmaceutical composition may be formulated and used as formulations for oral administration such as powders, granules, tablets, capsules, suspensions, emulsions, syrups or aerosol, ointment, suppositories, or sterile injection solutions by conventional methods, respectively, but is not limited thereto.

The pharmaceutical composition according to an embodiment of the present disclosure may be a drug composition or a quasi-drug composition.

Through the whole document, the term "quasi-drug" refers to an article having a milder action than drugs, among articles being used for the purpose of diagnosis, treatment, improvement, alleviation, handling or prevention of human or animal diseases. For example, according to the Pharmaceutical Affairs Law, the quasi-drugs are those, excluding articles used as drugs, including articles used for the purpose of treating or preventing human or animal diseases and articles which have a mild action on or have no direct influence on the human body.

In an embodiment of the present disclosure, the pharmaceutical composition may be administered in a pharmaceutically effective amount. Through the whole document, the term "pharmaceutically effective amount" refers to an amount sufficient to treat or prevent diseases at a reasonable benefit/risk ratio applicable to any medical treatment or prevention. An effective dosage level may be determined depending on factors including severity of the disease, drug activity, a patient's age, body weight, health conditions, gender, sensitivity to the drug, administration time, administration route, and excretion rate of the composition of the present disclosure, duration of treatment, drugs blended with or co-administered with the composition of the present disclosure, and other factors known in the medical field. The pharmaceutical composition of the present disclosure may be administered individually or in combination with an ingredient known for treating intestinal diseases. It is important to administer an amount to obtain a maximum effect in a minimum amount without side effects by considering all the above-described factors.

The pharmaceutical composition of the present application may be administered via, but not particularly limited to, intraperitoneal administration, intravenous administration, intramuscular administration, subcutaneous administration, intradermal administration, transdermal patch administration, oral administration, intranasal administration, intrapulmonary administration, rectal administration, etc. depending on the purpose.

However, when the pharmaceutical composition is administered via oral administration, it can be administered in an unformulated form, and since the strain(s) of the present disclosure can be denatured or degraded by gastric acid, the composition for oral administration may be coated with an active drug, formulated to be protected from degradation in the stomach, or formulated in the form or an oral patch. Also, the composition may be administered by any device capable of delivering an active ingredient to a target cell.

EXAMPLES

Example 1. Test to Verify Synergetic Effect of *Lactobacillus rhamnosus* LM1019 and Starter on Production of Nitric Oxide (NO)

In the present test, YO-MIX™ 207 obtained from Danisco was used as a starter, and the starter strains consist of *Streptococcus thermophilus, Lactobacillus delbrueckii* subsp. *bulgaricus, Lactobacillus acidophilus*, and *Bifidobacterium lactis*. To culture RAW 264.7 cells, mouse-derived macrophages, a DMEM culture medium (Welgene, Korea) comprising 10% fetal bovine serum (Welgene, Korea) and penicillin-streptomycin (Welgene, Korea) was used. The RAW 264.7 cells were seeded at a concentration of $3 \times 10^4$ cells/well in a 96 well plate and then cultured in a 37° $CO_2$ incubator for O/N.

After the medium was removed from each well, *Lactobacillus rhamnosus* LM1019 was diluted to $10^7$ CFU/mL and the starter strains were diluted to $10^5$ CFU/mL, $10^6$ CFU/mL, $10^7$ CFU/mL and $10^8$ CFU/mL, respectively, in the medium and treated for 24 hours. LPS was treated as a positive control. To measure the amount of nitric oxide produced, a Griess Reagent system from Promega was used. Then, 50 μl of the cultured medium was transferred to a new 96 well plate. To obtain a nitric oxide standard curve, a nitric oxide standard solution was used for dilution to 1.56 μM to 100 μM. Thereafter, 50 μl of a sulfanilamide solution was added to each well to react at room temperature while blocking light for 5 minutes. Each well was further added with 50 μl of an N-1-naphtylethylenediamine dihydrochloride (NED) solution to react at room temperature for 5 minutes while blocking light. Then, the absorbance at 540 nm was measured with a microplate reader, and the amount of nitric oxide produced was calculated using the nitric oxide standard curve.

As a result of the test, it was confirmed that when a group was simultaneously treated with $10^7$ CFU/mL of *Lactobacillus rhamnosus* LM1019 and $10^6$ CFU/mL of the starter strains, the amount of nitric oxide produced was 66.5% greater than the sum of the amounts of nitric oxide produced by groups treated with $10^7$ CFU/mL of *Lactobacillus rhamnosus* LM1019 and $10^6$ CFU/mL of the starter strains, respectively (see FIG. 1).

Example 2. Test to Verify Synergetic Effect of *Lactobacillus rhamnosus* LM1019 and Starter on TNF-α Secretion In the present test, YO-MIX™ 207 obtained from Danisco was used as a starter, and the starter strains consist of *Streptococcus thermophilus, Lactobacillus delbrueckii* subsp. *bulgaricus, Lactobacillus acidophilus*, and *Bifidobacterium lactis*.

RAW 264.7 cells were seeded at a concentration of $3×10^4$ cells/well in a 96 well plate and then cultured in a 37° $CO_2$ incubator for O/N. After the medium was removed from each well, *Lactobacillus rhamnosus* LM1019 and the starter strains were diluted to suitable cell densities, respectively, in the medium and treated for 24 hours. LPS was treated as a positive control. To check the amount of TNF-α secreted, a DuoSet® ELISA kit from R&D systems was used, and the amount of TNF-α secreted was measured according to the manufacturer's instructions. Then, the absorbance at 450 nm was measured with a microplate reader, and the amount of secreted TNF-α was calculated using a TNF-α standard curve.

Figure 2:
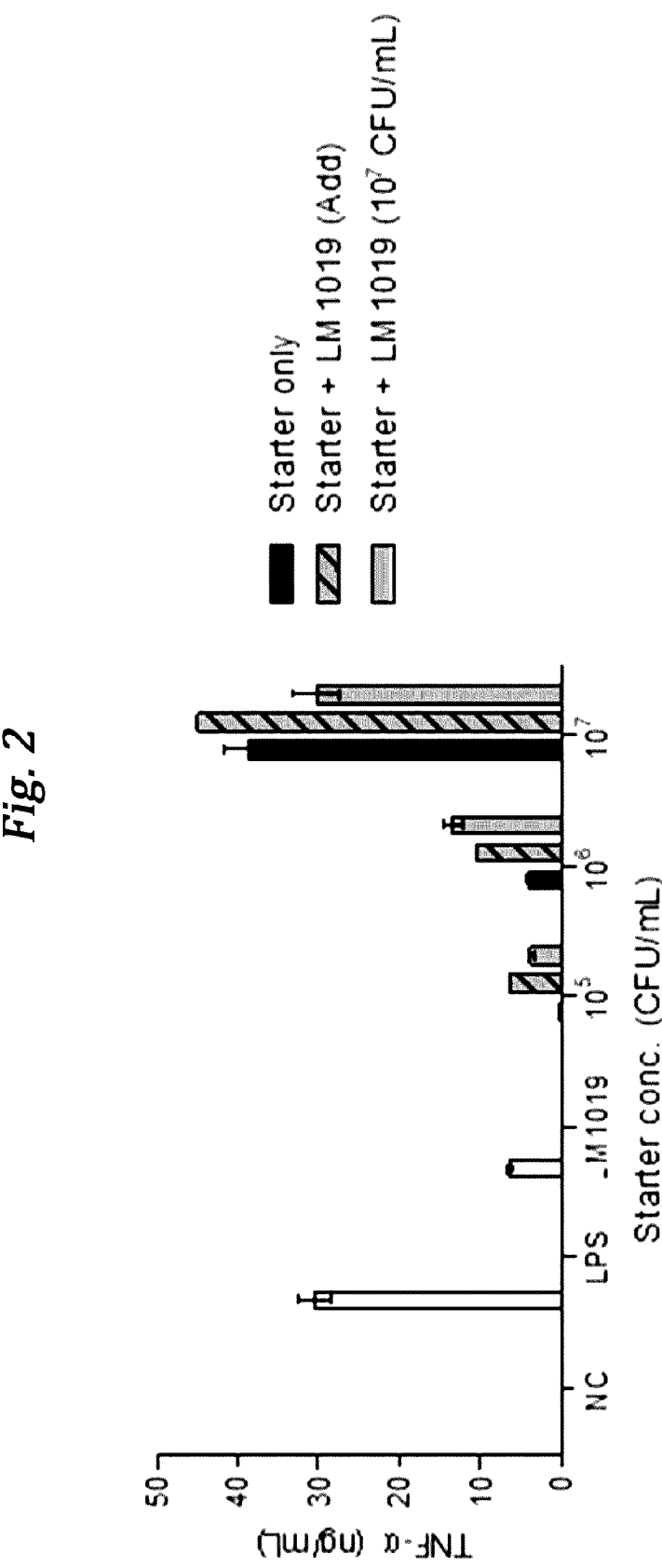
FIG. 2 shows the result of confirming the TNF-α secretion ability of *Lactobacillus rhamnosus* LM1019, starter strains, and mixtures thereof.

As a result of the test, it was confirmed that when a group was simultaneously treated with $10^7$ CFU/mL of *Lactobacillus rhamnosus* LM1019 and $10^6$ CFU/mL of the starter strains, the amount of secreted TNF-α was 28.1% greater than the sum of the amounts of TNF-α secreted by groups treated with $10^7$ CFU/mL of *Lactobacillus rhamnosus* LM1019 and $10^6$ CFU/mL of the starter strains, respectively (see FIG. 2).

To sum up, in both of the above immunity-related tests, the group simultaneously treated with $10^7$ CFU/mL of *Lactobacillus rhamnosus* LM1019 and $10^6$ CFU/mL of the starter strains showed an enhanced effect compared to the groups treated with $10^7$ CFU/mL of *Lactobacillus rhamnosus* LM1019 and $10^6$ CFU/mL of the starter strains, respectively, which confirmed that a mixture of $10^7$ CFU/mL of *Lactobacillus rhamnosus* LM1019 with $10^6$ CFU/mL of the starter strains has a synergetic effect on immunity.

The above description of the present disclosure is provided for the purpose of illustration, and it would be understood by a person with ordinary skill in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

We claim:

1. A composition comprising:
   a mixed strain of *Lactobacillus rhamnosus* LM1019 deposited under accession number KCCM12308P and starter strains,
   wherein the starter strains consist of *Streptococcus thermophilus, Lactobacillus delbrueckii* subsp. *bulgaricus, Lactobacillus acidophilus*, and *Bifidobacterium lactis*.

2. The composition of claim 1, wherein a concentration of *Lactobacillus rhamnosus* LM1019 deposited under accession number KCCM12308P in the mixed strain is $10^7$ CFU/mL, and a concentration of the starter strains in the mixed strain is $10^6$ CFU/mL.

3. The composition of claim 1, wherein the mixed strain increases the amount of nitric oxide produced.

4. The composition of claim 1, wherein the mixed strain increases the amount of secreted TNF-α.

5. An immune-enhancing food composition, comprising:
   a mixed strain of *Lactobacillus rhamnosus* LM1019 deposited under accession number KCCM12308P and starter strains, or a culture fluid or extracts of the mixed strain as an active ingredient,
   wherein the starter strains consist of *Streptococcus thermophilus, Lactobacillus delbrueckii* subsp. *bulgaricus, Lactobacillus acidophilus*, and *Bifidobacterium lactis*.

6. A pharmaceutical composition for preventing or treating immune-related diseases, comprising:
   a mixed strain of *Lactobacillus rhamnosus* LM1019 deposited under accession number KCCM12308P and starter strains, or a culture fluid or extracts of the mixed strain as an active ingredient,
   wherein the immune-related diseases include at least one selected from the group consisting of tuberculosis, pneumonia, peritonitis, urinary tract infection, meningitis, myopericarditis, encephalitis, measles, hepatitis, sepsis, bubonic plague, leprosy, syphilis, tetanus, anthrax, actinomycosis, botulism, *Clostridium difficile*-induced colitis, food poisoning, gas gangrene, tetanus, brucellosis, cholera, Legionnaires' disease, pertussis, bacillary dysentery, tularemia, typhoid fever, smallpox, chickenpox, shingles, COVID-19, SARS, MERS, dengue, yellow fever, Zika virus infection, Ebola virus disease, influenza, cold, avian influenza, hand-foot-mouth disease, acquired immunodeficiency syndrome (AIDS), and malaria; and
   the starter strains consist of *Streptococcus thermophilus, Lactobacillus delbrueckii* subsp. *bulgaricus, Lactobacillus acidophilus*, and *Bifidobacterium lactis*.

* * * * *